United States Patent [19]

Miller et al.

[11] Patent Number: 4,565,497
[45] Date of Patent: Jan. 21, 1986

[54] PUMP ACTUATOR

[75] Inventors: Phillip J. Miller, Berkeley; Jal S. Jassawalla, San Francisco, both of Calif.

[73] Assignee: Novacor Medical Corporation, Oakland, Calif.

[21] Appl. No.: 680,731

[22] Filed: Dec. 11, 1984

Related U.S. Application Data

[63] Continuation of Ser. No. 446,454, Dec. 3, 1982, abandoned.

[51] Int. Cl.⁴ .................. F04B 21/00; F04B 43/00; H02K 33/14; A61F 1/00
[52] U.S. Cl. ...................................... 417/63; 417/412; 310/33; 310/22; 128/10; 128/DIG. 3; 623/3
[58] Field of Search ................. 417/410, 412, 413, 63, 417/417–419; 310/33, 22, 29, 36; 73/722, 728; 318/127; 128/10, DIG. 3; 3/1.7

[56] References Cited

U.S. PATENT DOCUMENTS

| | | |
|---|---|---|
| 1,893,776 | 1/1933 | Hull . |
| 2,228,565 | 1/1941 | Haddaway ........................ 417/412 |
| 2,429,441 | 10/1947 | Williams .......................... 417/413 |
| 2,816,514 | 12/1957 | Freese . |
| 2,949,775 | 8/1960 | Newbold ......................... 73/722 X |
| 3,263,105 | 7/1966 | Heyek . |
| 3,308,361 | 5/1967 | Nakai et al. . |
| 3,515,966 | 6/1970 | De Valroger et al. ............. 318/127 |
| 3,633,217 | 1/1972 | Lance . |
| 3,867,675 | 2/1975 | Kitz et al. ....................... 318/127 X |
| 3,963,380 | 6/1976 | Thomas, Jr. et al. . |
| 4,167,046 | 9/1979 | Portner et al. . |
| 4,384,829 | 5/1983 | Conley et al. ...................... 92/50 X |

FOREIGN PATENT DOCUMENTS 260233  6/1970  U.S.S.R. ................................ 73/728

*Primary Examiner*—Carlton R. Croyle
*Assistant Examiner*—Theodore W. Olds
*Attorney, Agent, or Firm*—Fitch, Even, Tabin & Flannery

[57] ABSTRACT

An actuator is described for use in a pump having a pump chamber whose contents are expelled by movement of a pair of pusher plates toward one another. The actuator includes opposed solenoid armatures which are operable for movement between open and closed positions. The armatures are each operatively connected to an associated pusher plate by a main spring which is attached at one end to the back end of the armature, extends through a front-to-back slot in an armature core, and is connected at its opposite end to the pusher plate. A pair of preload springs carried on each armature and disposed on either side of the associated main spring acts to hold the main spring in a prestressed condition prior to solenoid actuation. With closure of the armatures, and with the sac still in an expanded condition, the main springs are disengaged from the associated preload spring and placed in a more stressed, more planar configuration, with the increased stress in each main spring being relieved by movement of the pusher plates toward one another.

7 Claims, 6 Drawing Figures

PUMP ACTUATOR

This is a continuation of application Ser. No. 446,454, filed Dec. 3, 1982 and now abandoned.

BACKGROUND AND SUMMARY

The present invention relates to an actuator mechanism for a pump, and in particular, to an improved actuator mechanism for use in an internally implantable blood pump or the like.

A variety of different types of heart replacement and heart-assist pumps have been proposed in the prior art. One type of pump which offers advantages in size, weight and reliability is a so-called deformable-sac pump, in which a pair of opposed pusher plates are movable reciprocally from relatively more displaced positions to relatively less displaced positions for expelling the fluid contents of a deformable sac. By way of example, a pump of this general type is shown and described in U.S. Pat. No. 4,167,046. Briefly the device described therein includes a disk-like deformable sac having an annular side wall supported in a rigid condition and a pair of opposed movable walls against which the reciprocally movable pusher elements act. Various advantages inherent in this construction are set forth in the aforementioned patent.

The actuator which is used in a deformable-sac pump of the type just described operates to move the opposed pusher plates recurrently from their more displaced to their less displaced positions, preferably in a manner which produces controlled-rate, synchronous plate movement. At the same time, the actuator must be efficient, relatively smooth working, and reliable over long periods of continued use. One type of actuator which provides a number of advantages in a deformable-blood sac has been described in U.S. patent application for Pump and Actuator Mechanism, Ser. No. 211,210, filed Nov. 28, 1980, and assigned to the assignee of the present application.

The actuator disclosed in the just-mentioned application includes a solenoid device which operates between open and closed positions to produce increased bending in opposed prestressed beam springs which operatively connect opposed armatures in the actuator to associated pusher plates. The increased bending in the springs is released by movement of the two pusher plates inwardly toward their less displaced end-of-stroke positions. An important feature of the actuator is that the beam springs, in acting between less stressed and more stressed conditions, produce a relatively flat output force profile in acting against the associated pusher plates. As a result, peak loads on the pump components are minimized. The actuator, having few moving parts, is also simple in construction and operation, and is therefore quite reliable over long periods of continued use.

The present invention contemplates an improved actuator which incorporates many of the advantageous features of the actuator just described, and further includes a number of unique and hitherto unknown features which enhance pump reliability and operational characteristics and contribute to compactness in the pump design.

Accordingly, one object of the present invention is to provide an actuator for use in a deformable-sac type implantable blood pump, where the actuator is quite compact.

Another object of the invention is to provide such an actuator having highly reliable and predictable performance characteristics.

It is yet another object of the invention to provide such an actuator whose operation can be accurately monitored and controlled.

The actuator of the invention includes an armature which is mounted for movement between open and closed positions, and which includes a solenoid core defining an internal front-to-back slots. An elongate main spring in the actuator is attached at one spring end to the back region of the armature, extends through the core slot, and is attached at its other end to a pusher element adapted to act against a deformable sac. An elongate preload spring connected at one of its ends to the armature and operatively connected at its other end to the main spring functions to support the main spring in a relatively less stressed condition when the armature is in its open position.

In a preferred embodiment of the invention, the main spring includes a plate-like spring which is curved in the direction of its action on the pusher element, and is in a more planar configuration when in its relatively more stressed condition.

Also in a preferred embodiment of the invention, the actuator includes a symmetrical arrangement of components acting on opposed pusher elements to compress the sac symetrically from opposite sides. The actuator may further include position sensors for monitoring solenoid armature and/or main spring positions, to provide data used in controlling the operation of the actuator.

These and other objects and features of the present invention will become more fully apparent when the following detailed description of a preferred embodiment of the invention is read in conjunction with the accompanying drawings.

DETAILED DESCRIPTION OF A PREFERRED EMBODIMENT OF THE INVENTION

Figure 1:
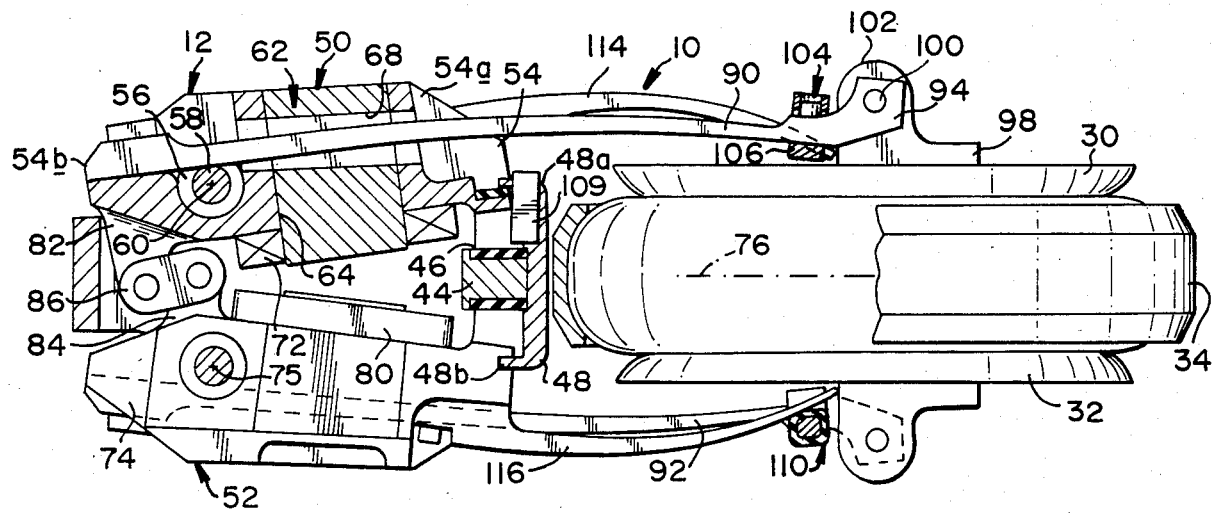
FIG. 1 is a side, partially cross-sectional schematic view of a pump employing an actuator constructed in accordance with the invention.

FIGS. 1–4 illustrate an implantable blood pump 10 which is driven by an actuator, or actuator mechanism, 12 constructed according to the present invention. The pump generally includes a deformable sac 14 having an annular side wall 16 (FIGS. 2 and 3) and a pair of opposed circular movable walls 18, 20 each of which is joined to the side wall through an annular flexible wall portion, such as wall portion 22 adjoining wall 18 to wall 16. The sac, which is also referred to as a flexible enclosure, defines an internal variable-volume pump chamber 24. In pump operation, fluid such as blood is supplied to the pump chamber through a valved inlet conduit 26, shown fragmentarily in FIG. 4, and is expelled under pressure, through a valved outlet conduit, shown fragmentarily at 28 in FIG. 4.

The pump includes opposed pusher elements, or pusher plates 30, 32 which are attached to, and substantially cover, sac walls 18, 20, respectively. The two pusher plates are movable, under the control of actuator 12, from initial, start-of-stroke positions shown in FIG. 1 inwardly and synchronously, to end-of-stroke positions shown in FIG. 3. Such plate movement causes fluid in chamber 24 to be expelled from the pump, through outlet conduit 28.

The central portions of the sac, including side wall 16 and the inlet and outlet conduits formed therewith, are encased in a rigid housing 34. As can be appreciated in FIGS. 2 and 3, the housing functions to support the sac side wall in a stationary position as walls 18, 20 are moved toward and away from one another during pumping action. The rigid housing is also used in attaching actuator 12 rigidly to the pump chamber.

Figure 3:
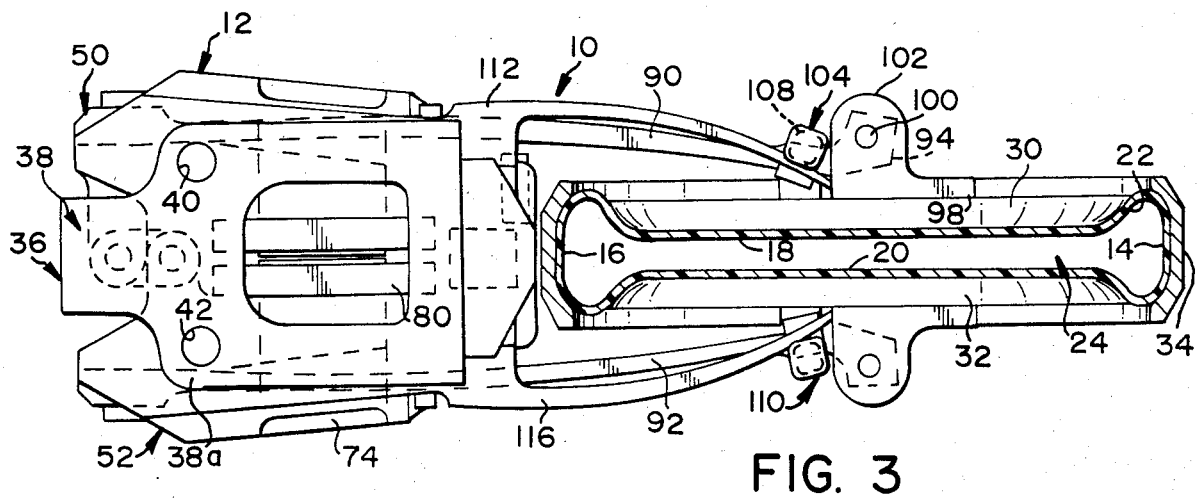
FIG. 3 is a view similar to FIG. 1, with other actuator parts added, illustrating a third condition of the pump.
Figure 4:
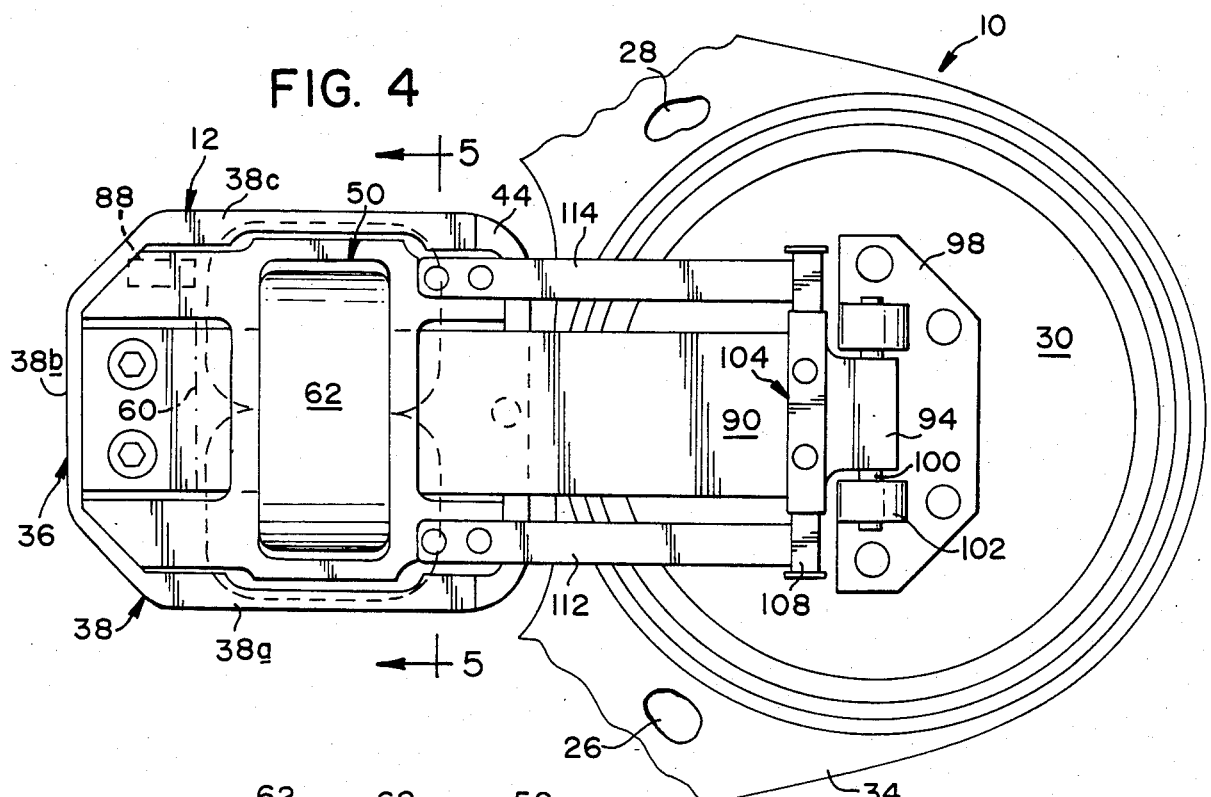
FIG. 4 is a top view of the pump shown in FIGS. 1–3.

Considering now details of actuator 12, a frame 36 in the actuator includes a generally U-shaped frame member 38, a side 38a of which is seen in FIG. 3, and the three sides 38a, 38b and 38c of which are seen in top view in FIG. 4. Opposed parallel sides 38a, 38c in the frame member are provided with pairs of aligned bores, such as the pair including bore 40, and the pair including bore 42, both in side 38a, (FIG. 3).

Figure 2:
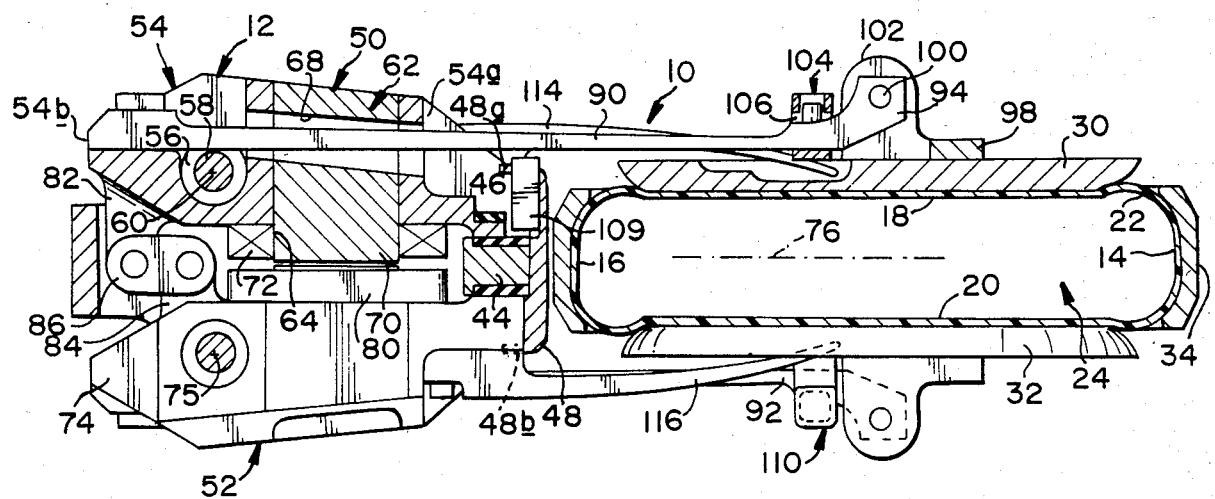
FIG. 2 is a view like FIG. 1, with additional parts cut away, illustrating a second condition of the pump.

A front frame plate 44 seen sectionally in FIGS. 1 and 2, and in top view in FIG. 4 extends between the open sides of the frame member and is secured thereto as by bolting. The upper and lower surfaces of plate 44 are provided with energy absorbing pads, such as pad 46, which serve a purpose to be described. The pads are preferably formed of rubber, polyurethane, or other resilient pad material. Also attached to the frame plate is a stop member 48 having opposed, rearwardly projecting stops 48a, 48b seen in FIGS. 1 and 2.

The actuator includes a pair of solenoid armatures 50, 52 mounted on the frame for pivoting between open and closed positions which are shown in FIGS. 1 and 2, respectively. Armature 50, which is representative, comprises an armature support 54 whose front and back end regions are indicated at 54a, 54b, respectively, in FIG. 1. The armature support is pivotally mounted on frame 36 by a pin 58 which extends through the pair of aligned frame bores which includes bore 40, and is received in bearings, such as bearings 56 held in the armature support. The pivot axis, indicated by dashed-dot line 60 in FIG. 4, is normal to the direction of movement of the two pusher plates and is also normal to the plane of FIGS. 1–3.

Figure 5:
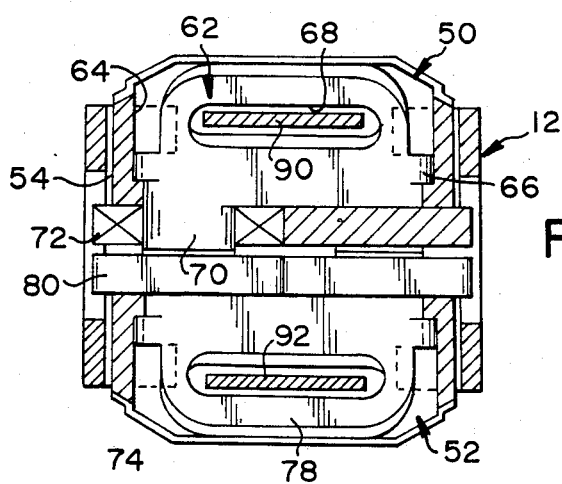
FIG. 5 is a sectional view taken generally along line 5—5 in FIG. 4.

Also included in armature 50 is a C-shaped solenoid core 62 having the general shape seen in side view in FIGS. 1 and 2 and front-on in FIG. 5. It can be seen in FIG. 5 that the core is received within a central cavity 64 formed in the support member, with a pair of opposed side projections in the core, such as projection 66, being received against side shoulder portions in the cavity. According to an important feature of the invention, core 62 is provided with an elongate slot 68 extending in a front-to-back direction as seen in FIGS. 1 and 2. The slot serves a purpose which will be described below. Core 62, which is conventionally bonded to the support member, is formed of a suitable ferromagnetic material such as an iron-cobalt-vanadium alloy.

Each of the two inwardly extending poles in the core, such as pole 70, is wrapped with a conductive-wire winding, or coil, such as coil 72 seen cross sectionally in FIG. 5. The lead wires of the two coils in the core are connected to an actuator control device (not shown) which controls the operation of the actuator in a manner which will be detailed below.

Likewise armature 52 comprises an armature support 74 which is mounted on frame 36 for pivoting about an axis 75 defined by the aligned pair of frame bores which includes bore 42 in FIG. 3. Axis 75 is parallel to axis 60, and the two axes are equidistant from a mirror image plane which bisects the pump sac axially, and which is indicated by dashed-dot line 76 in FIGS. 1 and 2. Armature 52 also includes a solenoid core 78 having a pair of windings, such as winding 80 seen in FIGS. 1–3, whose lead wires are connected to the above-mentioned control unit. The core windings in the two armatures are energized from a storage capacitor, or by other suitable means in the control unit to set up magnetic fields in the two cores which draw the two armatures together, from their open positions shown if FIG. 1 toward their closed positions shown in FIG. 2.

As the two armatures approach their closed positions, the armature supports make initial, cushioned contact with associated pads, such as pad 46, on plate 44 as seen in FIG. 2. These pads cushion solenoid closure at the closed positions of the two armatures, and define a residual solenoid gap between the confronting poles in cores 62, 78. Specifically, the pads are constructed and dimensioned to prevent actual contact between the two cores with solenoid closure. The open, unenergized positions of the armatures are determined by the positions of the associated pump pusher plates.

The actuator also includes a mechanical linkage between the two armatures for constraining the armatures to move toward and away from one another symetrically with respect to the mirror-image plane represented by line 76. This linkage includes a linkage arm 82 formed on the back end of armature support 54, and a more forwardly disposed linkage arm 84 formed on support 74. A connecting link 86 pivotally joins the two arms through pivot pins which are seen cross sectionally in FIGS. 1 and 2. It can be appreciated with reference to the latter figures, that as one of the armatures, for example armature 50, pivots toward its closed positions, movement of arm 82 acts on arm 84 through link 86 to move the other armature substantially the same amount toward its closed position. Similarly, the two armatures move in a symetrical, coordinated manner when moving from their closed toward their open positions.

The actuator is also provided with a pair of armature position detectors, such as the detector shown schematically in dashed outlines at 88 in FIG. 4. Preferably each detector is a conventional eddy current type detector which operates to measure the spacing between a current-signaling surface and a target surface, according to current changes produced by magnetic induction in the target surface. In the particular construction herein, each detector is suitably mounted on the rear part of frame 36 to interact with a target surface formed on the associated armature support. The two detectors are operable to provide accurate instantaneous data as to the positions of the associated armatures, as these move between their open and closed positions. The detector position data is supplied to the above-mentioned control device, to provide control feedback information to the control unit during solenoid actuation.

Armatures 50, 52 are operatively connected to associated pusher plates 30, 32 by main springs 90, 92, respectively. Spring 90, which is representative, includes an elongate plate or ribbon-like spring which is seen in side view in FIG. 1-3 and in plan view in FIG. 4. The back end of the spring is attached as by bolting to the back end of armature support 54. According to an important feature of the present invention the spring extends through slot 68 formed in armature core 62, as seen in FIGS. 1 and 2. As seen in FIG. 5, the width of the spring extends along a major portion of the length of the slot. The right end of the main spring in FIGS. 1-4 terminates at an enlargement 94 having a bore formed axially (normal to the long axis of the spring) therein. A pillow block 98 is attached as by bolting to pusher plate 30, as seen best in FIG. 4. The main spring is pivotally attached to the pillow block by a pivot pin 100 extending through the spring enlargement bore and through bores formed in a pair of mounts, such as mount 102 in the pillow block.

A preload stop member 104 associated with mainspring 90 includes a central slotted portion 106 through which the main spring is received and at which the stop member is secured to the main spring as by bolting. The central portion is seen cross sectionally in FIGS. 1 and 2. Member 104 has a pair of axially opposed preload stops, such as stop 108, each having the general rectangular shape in cross section seen in FIG. 3.

The main spring is formed of a suitable spring material such as titanium, steel, a fiber composite or the like and is curved, in a relaxed, or unstressed condition in the direction of its action on pusher plate 30, i.e., inwardly on progressing away from the spring's attachment to the armature. As will be seen below with reference to the described operation of the actuator, the curvature of spring 90 seen in FIG. 1 (and the substantially mirror-image curvature of spring 92) represent the curvature in the spring with such in a relatively less-stressed condition. This curvature is somewhat less than that of the main spring in a totally unstressed or relaxed condition.

The spacing between an inner surface portion of spring 90 and frame 36 is monitored by a position detector 109 similar to the eddy current armature position detectors described above.

The construction of spring 92 and its attachment at one end to armature 52 and at its other end to an associated pusher plate 32 through a pillow block is similar to what has already been described with reference to main spring 90. Also a stop member 110 in the actuator is like stop member 104 in its construction and attachment to the associated main spring.

Completing the description of the actuator, there is associated with each main spring, such as main spring 90, a pair of preload springs, such as springs 112, 114, disposed on either side of the associated main spring as seen in FIG. 4. The preload springs are attached, as by bolting, to the front end region of support 54 and are dimensioned to contact associated stops, such as stop 108, in the stop member as can be appreciated particularly in FIG. 3. According to an important feature of the present invention, the preload springs have a selected curvature and spring constant which, with the pump in the condition shown in FIG. 1, that is, with the solenoid armatures in their open positions, and the pusher plates in their relatively more displaced positions, act to bend spring 90 from its more curved, relaxed position to a less curved condition seen in FIGS. 1 and 3. The action of the preload springs against the main spring, of course, bends the preload springs inwardly somewhat from their relaxed, unstressed positions.

Similar preload springs, such as spring 116 seen in FIGS. 1-3, function to hold main spring 92 in a relatively less'stressed position, with the pump in the figuration shown in FIG. 1, which is a mirror image of the less stressed condition main spring 90. The pair of preload springs associated with each main spring is also referred to herein as preload means. Such means may also include relatively rigid elongate members.

In this condition, each main spring in the actuator is held in its relatively less stressed position by the action of the associated preload springs acting against the stop member on that main spring. Specifically, the preload springs act in an outwardly direction to move the associated main spring from a maximally curved configuration outwardly (away from the mirror image plane in the pump) to the position shown in solid lines in FIG. 1.

The operation of the pump and particularly the operation of the actuator therein may be observed sequentially in FIGS. 1-3. FIG. 1 illustrates the pump in a start-of-stroke condition in which pump sac 14 is filled and solenoid armatures 50, 52 are in their open, unenergized positions. The pump ejection stroke is initiated by the control unit, typically with the supply of current to the windings in the armatures from a storage capacitor in the control unit. When energized, the armatures are drawn toward one another, symmetrically with respect to the mirror image plane in the pump, and at a rate which may be controlled by varying the instantaneous current supplied to the windings.

FIG. 2 shows the condition of the pump immediately after solenoid closure. At this point, the inertia of the filled pump chamber retains the ends of positions as in FIG. 1. At the same time, the preload springs are moved inwardly with the armatures, out of contact with the stops on the main springs, and the main springs are placed in relatively more stressed, more planar configurations illustrated in solid lines in FIG. 2. Thus, the energy used in solenoid closure is used initially to produce a greater loading in the main springs, whereby they contain greater stored energy.

After initial solenoid closure, the armatures therein may be held in their closed positions by a relatively small latching current supplied by the control unit. If additional holding force is needed, a small permanent magnet may be used. The force of the latter may be overcome, in returning the armatures to their open positions, by a small reverse current in the solenoid windings.

If the energizing means used to hold the armatures in their closed positions inadvertantly fails, with the pusher plates still in their relatively more spaced positions, the relatively greater stress in the main springs may act to open the armatures rapidly beyond their usual open positions. When this occurs, contact between the armatures and associated stops 48a, 48b acts to limit armature "overshoot" to positions only slightly beyond such open positions, and to dampen oscillatory motion in the armatures.

From the condition shown in FIG. 2, the tendency of the two main springs to relieve the stressed condition therein results in plates 30, 32 being moved toward each other, thus expelling contents of the pump chamber and producing the desired pumping action in the pump. It can be appreciated that as the pusher plates approach their end-of-stroke positions shown in FIG. 3, the main springs are again positioned to make contact with the associated preload springs through the stops on the main springs. Immediately after contact of the main spring preload stops with the associated preload springs, a portion of the stored loading energy in the main springs is imparted to the preload springs, bending the latter inwardly until the force and counterforce exerted by the main spring and the preload springs, respectively, are equalized. At this point, the main springs are again in the relatively less stressed, more curved conditions described with respect to FIG. 1. Once this has occurred, the solenoid coils are deenergized or unlatched.

The apparatus is returned to the condition described with respect to FIG. 1 as a result of filling of the sac, as by cardiac systole. This filling may take place passively, wherein movement of the pusher plates outwardly to their relatively more spaced positions is accommodated by pivoting of the armatures toward their open positions.

The positions of the pusher plates during the just-described pumping operation may be monitored by position detector 109 which inputs the control unit. Specifically, at the point where the two pusher plates reach their most inwardly moved position, the control unit in the pump may respond to a minimum threshold spacing signal or to a minimum threshold rate of change signal from the detector to release the latching current in the pump to allow pump filling to occur. During pump filling, as the pump returns from its FIG. 3 condition to its FIG. 1 condition, either the detector 105 or the armature position detectors, or both, may signal the control unit, as to a threshold spacing or threshold rate of movement condition which occurs when the pump chamber is filled, and the pump is ready to resume its pumping function.

Figure 6:
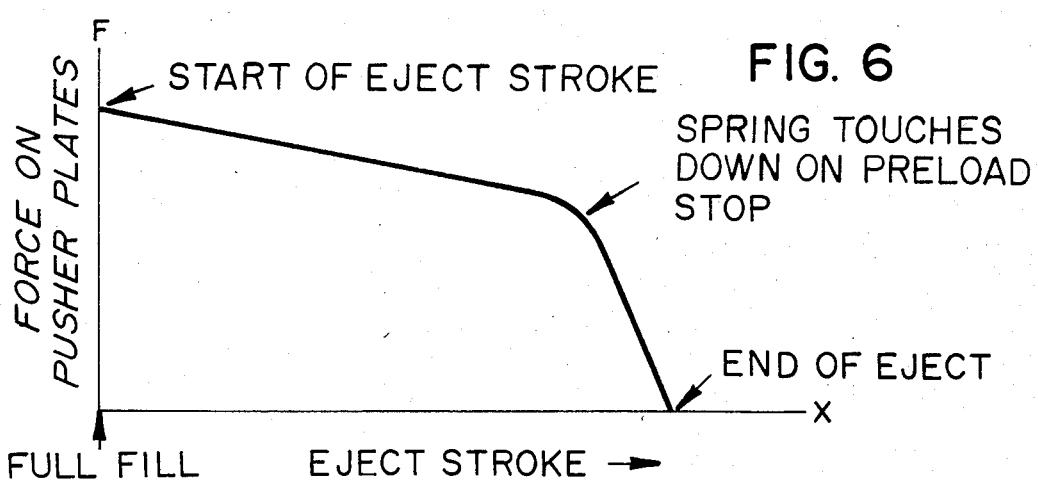
FIG. 6 is a graph illustrating the force exerted on a pusher plate in the pump by an associated spring beam in the actuator, as a function of the position of the pusher plate between start-of-stroke and end-of-stroke positions.

FIG. 6 is a graph of the force curve which characterizes the force of a pusher plate, such as plate 30, acting against the associated sac wall during pumping action. The left-hand edge of the curve represents the start of the eject stroke, represented by the FIG. 2 condition of the pump just after solenoid closure. The nearly horizontal portion of the curve between the start of the eject stroke and the point at which the spring makes contact with the preload stop is the normal characteristic of stress relief in a beam spring between relatively more and relatively less stressed conditions. Each main spring is selected to have a relatively low spring constant so that this portion of the curve is as horizontal as possible. After the main spring makes contact with the preload springs, the force of the pusher plate acting against the sac falls relatively quickly to a zero level as stored energy in the spring is given up to the preload springs and the main spring comes to rest in its relatively less stressed condition.

The construction and operation of the invention has been described above with reference to an actuator having a pair of opposed main springs which are under the control of a pair of coordinately movable armatures. The invention also contemplates an actuator adapted for driving an asymetric deformable pump sac in which the pumping action is achieved by recurrently moving a single pusher plate against a deformable sac surface. Such actuator includes a single armature, like armature 50, connected to the pusher plate operatively by a main spring, such as main spring 90, this being held in a relatively less stressed position during nonpumping phases of the pump operation by one or more preload springs which act on the main spring in the manner described above.

From the foregoing, it can be seen how the various objects of the present invention are met. The invention provides the advantageous features of the pump actuator mechanism described in the above-mentioned patent application for Pump and Actuator Mechanism Ser. No. 211,210. These advantages include mechanical simplicity, and greater efficiency and reliability inherent in the operation of a beam spring acting between relatively less stressed and relatively more stressed conditions and directly coupled to a solenoid armature and a pusher plate acting on a deformable sac.

The present invention provides additional advantages which are not present in pump actuators disclosed in the prior art. One important advantage is that the unique armature construction, and in particular, the slotted armature core in the actuator, allows the armature to be operatively coupled to the associated pusher plate by a single, relatively wide main spring extending from the back of the armature through the solenoid core slot to its point of attachment on the pusher plate. A significant advantage in the use of the single main spring is that problems of matching the spring constant characteristics of two or more springs working in parallel are avoided, as are problems of nonuniform changes in spring performance characteristics over extended periods of pump use.

The actuator construction also allows for greater compactness. In this regard, it is noted that the placement of a portion of the main spring within the solenoid core in the armature permits the main spring to be disposed relatively close to the mirror image plane in the actuator. Further, the inward curvature of the main spring and the preload springs in the actuator act to reduce overall pump thickness.

Symmetry of pump design and operation largely eliminates loads between the actuator and the pump housing. The linkage mechanism insures that movement of the armatures is symmetrical, particularly during pump filling. Because the armatures operate in a symmetrical manner, information about the position of one armature can be used to provide accurate position information as to both armatures.

While a preferred embodiment of the invention has been described herein, it will be appreciated by those skilled in the art that various changes and modifications can be made without departing from the spirit of the invention.

What is claimed is:

1. In a pump having a flexible enclosure defining a pump chamber, and a pair of opposed substantially axially aligned pusher elements engaged with opposed movable walls in the enclosure for movement between first relatively more spaced positions and second relatively less spaced positions to expel fluid from the enclosure, an actuator for producing coordinated movement of the pusher elements between their first and second positions, comprising:

a frame, a pair of armatures, each having front and back end regions, and mounted on said frame for movement between open relatively more spaced and closed relatively less spaced positions, substantially in the direction of movement of the elements toward and away from each other, and with the armatures' front end regions being disposed adjacent the enclosure, a solenoid core in each armature, said solenoid cores being energizeable to cause said armatures to move from their open positions to their closed positions, a pair of opposed, elongate main springs, each attached at one spring end to an associated armature and being attached at its other spring end to an associated pusher element, said main springs being arranged on opposite sides of the flexible enclosure and having their longitudinal axes substantially coplanar with the axes of the pusher elements, said main springs further being arranged within the outermost dimension of said armatures in the direction of the axes of the pusher elements, and elongate preload means associated with each of said main springs, each of said preload means having one end connected to the associated armature and having its other end arranged for operative engagement with the associated main spring for holding said main spring in a relatively less stressed condition with the pusher element in its first position, and with said armature in its open position, said armatures being movable to their closed positions with the pusher elements still in their first positions to disengage said preload means from said associated main springs and bend the main springs to relatively more stressed second conditions, whereby in relieving the increased stress in said main springs, said other ends of said main springs are displaced to move the pusher elements coordinately toward their second, relatively less spaced positions, said solenoid cores each having a front-to-back slot therein with a respective one of said main springs extending through said slot, said slots each being of a size sufficient to provide clearance between each of said cores and the associated one of said main springs for all said operative positions of said armature and all said operative conditions of said spring.

2. The actuator of claim 1, wherein each main spring includes a plate-like spring which, in its relatively less stressed condition, is curved in the direction of its action on the associated element, and in its relatively more stressed condition, is relatively more planar.

3. The actuator of claim 1, wherein each of said preload means includes a pair of springs disposed on either side of the associated main spring.

4. The actuator of claim 1, which further includes position detector means for measuring the spacing between said armatures throughout movement between their open and closed positions.

5. The actuator of claim 4, wherein said position detector means includes means for determining the spacing between said frame and a reference point on one of said armatures.

6. The actuator of claim 1, which further includes position detector means for detecting the position of at least one pusher plate by measuring the spacing between the associated main spring and said frame throughout relative movement therebetween.

7. The actuator of claim 1, wherein said armatures are mounted on said frame for pivoting about spaced parallel axes, and are pivotly connected to one another to produce substantially symmetrical, coordinated movement of the armatures with respect to a plane disposed midway between, and normal to the plane containing, said axes.

* * * * *

UNITED STATES PATENT AND TRADEMARK OFFICE
CERTIFICATE OF CORRECTION

PATENT NO. : 4,565,497
DATED : January 21, 1986
INVENTOR(S) : Phillip J. Miller, et al.

It is certified that error appears in the above-identified patent and that said Letters Patent is hereby corrected as shown below:

Column 2, line 10, "slots" should be --slot--.
Column 6, line 38, after "ends of", insert --the main springs essentially in the same axially spaced--.

Signed and Sealed this

Seventeenth Day of June 1986

[SEAL]

Attest:

DONALD J. QUIGG

Attesting Officer

Commissioner of Patents and Trademarks